US010213486B2

(12) United States Patent
Carter et al.

(10) Patent No.: US 10,213,486 B2
(45) Date of Patent: Feb. 26, 2019

(54) FORMULATIONS OF DILUTED AMINO ACID SEGMENTS AND METHODS FOR MAKING SAME

(71) Applicant: Deseret Biologicals, Inc., Sandy, UT (US)

(72) Inventors: Jacob L. Carter, Pleasant Grove, UT (US); Edwin Douglas Lephart, Orem, UT (US)

(73) Assignee: Deseret Biologicals, Inc., Sandy, UT (US)

( * ) Notice: Subject to any disclaimer, the term of this patent is extended or adjusted under 35 U.S.C. 154(b) by 0 days.

(21) Appl. No.: 15/470,239

(22) Filed: Mar. 27, 2017

(65) Prior Publication Data

US 2017/0196939 A1 Jul. 13, 2017

Related U.S. Application Data

(62) Division of application No. 13/428,907, filed on Mar. 23, 2012, now Pat. No. 9,603,898.

(60) Provisional application No. 61/466,638, filed on Mar. 23, 2011.

(51) Int. Cl.
| | | |
|---|---|---|
| *A23L 2/52* | (2006.01) | |
| *A23L 7/10* | (2016.01) | |
| *A61J 1/03* | (2006.01) | |
| *A61J 1/05* | (2006.01) | |
| *A61K 9/00* | (2006.01) | |
| *A61K 9/08* | (2006.01) | |
| *A61K 9/19* | (2006.01) | |
| *A61K 9/20* | (2006.01) | |
| *A61K 9/48* | (2006.01) | |
| *A23L 33/10* | (2016.01) | |
| *A61K 38/18* | (2006.01) | |
| *A61K 38/22* | (2006.01) | |
| *A61K 47/10* | (2017.01) | |
| *B65D 23/14* | (2006.01) | |

(52) U.S. Cl.
CPC .............. *A61K 38/22* (2013.01); *A23L 2/52* (2013.01); *A23L 7/10* (2016.08); *A23L 33/10* (2016.08); *A61J 1/03* (2013.01); *A61J 1/05* (2013.01); *A61K 9/0053* (2013.01); *A61K 9/0056* (2013.01); *A61K 9/0095* (2013.01); *A61K 9/08* (2013.01); *A61K 9/19* (2013.01); *A61K 9/20* (2013.01); *A61K 9/48* (2013.01); *A61K 38/18* (2013.01); *A61K 47/10* (2013.01); *B65D 23/14* (2013.01); *A23V 2002/00* (2013.01)

(58) Field of Classification Search
CPC ............ A61K 38/2013; A61K 38/2086; A61K 47/48023; A61K 47/48215; A61K 47/48423; A61K 47/48507; A61K 47/48784; A61K 47/60; A61K 47/6835; C07K 2319/30
See application file for complete search history.

(56) References Cited

U.S. PATENT DOCUMENTS

| | | | |
|---|---|---|---|
| 4,911,897 A | 3/1990 | Alphonse | |
| 5,162,037 A | 11/1992 | Whitson-Fischman | |
| 5,603,915 A | 2/1997 | Nelson et al. | |
| 5,629,286 A | 5/1997 | Brewitt | |
| 5,683,712 A | 11/1997 | Cavazza | |
| 5,795,573 A | 8/1998 | Paradise | |
| 5,797,839 A | 8/1998 | Herscu | |
| 6,024,734 A | 2/2000 | Brewitt | |
| 6,142,927 A | 11/2000 | Clark | |
| 6,239,105 B1 | 5/2001 | Brewitt | |
| 6,331,610 B1 * | 12/2001 | Bourinbaiar ........... A61K 38/24 530/324 |
| 6,471,971 B1 | 10/2002 | Wollenweber et al. | |
| 6,485,480 B1 | 11/2002 | Brewitt | |
| 7,229,648 B2 | 6/2007 | Dreyer | |
| 7,923,040 B2 | 4/2011 | Dreyer | |
| 8,097,596 B2 | 1/2012 | Dale | |
| 9,603,898 B2 * | 3/2017 | Carter ................. A61K 38/18 |
| 2002/0010391 A1 | 1/2002 | Herscu | |
| 2002/0025314 A1 | 2/2002 | Etienne | |
| 2002/0049422 A1 | 4/2002 | Brewitt | |
| 2002/0059247 A1 | 5/2002 | Dillinger et al. | |
| 2002/0071873 A1 | 6/2002 | Brewitt | |
| 2002/0160051 A1 | 10/2002 | Lablanchy | |
| 2002/0168631 A1 | 11/2002 | Park et al. | |
| 2003/0022206 A1 | 1/2003 | Kay et al. | |

(Continued)

FOREIGN PATENT DOCUMENTS

| | | |
|---|---|---|
| BR | PI9405319-7 | 12/1996 |
| DE | 199 40 748 | 3/2001 |

(Continued)

OTHER PUBLICATIONS

Petit et al. Effect of Homeopathic Dilutions on Subcellular Enzymatic Activity. Human Toxicol. vol. 8, pp. 125-129. (Year: 1989).*

(Continued)

*Primary Examiner* — Marcela M Cordero Garcia
(74) *Attorney, Agent, or Firm* — Holland & Hart, LLP

(57) ABSTRACT

A formulation of a diluted amino acid fragment is prepared by mixing an amino acid fragment and a diluting agent to form a mixture. The mixture is serially diluted to produce a diluted formulation. The amino acid fragment includes a peptide sequence that is the same as a portion of a longer peptide sequence found in a naturally occurring material. A homeopathic remedy can be prepared using the formulation.

31 Claims, No Drawings
Specification includes a Sequence Listing.

(56) References Cited

U.S. PATENT DOCUMENTS

| | | |
|---|---|---|
| 2003/0191061 A1 | 10/2003 | Brewitt |
| 2004/0019107 A1 | 1/2004 | Taub et al. |
| 2004/0180101 A1 | 9/2004 | Dreyer |
| 2005/0100513 A1 | 5/2005 | Watkins et al. |
| 2005/0214243 A1 | 9/2005 | Fleming |
| 2005/0214244 A1 | 9/2005 | Fleming |
| 2006/0045918 A1 | 3/2006 | Jonas et al. |
| 2006/0045919 A1 | 3/2006 | Jonas |
| 2006/0069057 A1 | 3/2006 | Seinfeld |
| 2006/0088575 A1 | 4/2006 | Brewitt |
| 2006/0134202 A1 | 6/2006 | Hack et al. |
| 2007/0055113 A1 | 3/2007 | Quinn |
| 2007/0141169 A1 | 6/2007 | Taub et al. |
| 2007/0154499 A1 | 7/2007 | Fleming |
| 2007/0212406 A1 | 9/2007 | Taub et al. |
| 2008/0039523 A1 | 2/2008 | Albert et al. |
| 2008/0095801 A1 | 4/2008 | Weineck |
| 2008/0146677 A1 | 6/2008 | Warnock et al. |
| 2008/0234214 A1 | 9/2008 | Dale et al. |
| 2008/0254071 A1 | 10/2008 | Taraborrelli et al. |
| 2008/0279902 A1 | 11/2008 | Luria et al. |
| 2009/0136599 A1 | 5/2009 | DeAmorim |
| 2009/0186080 A1 | 7/2009 | Banks |
| 2009/0191242 A1 | 7/2009 | Delbosc et al. |
| 2009/0232904 A1 | 9/2009 | Quinto et al. |
| 2010/0221332 A1 | 9/2010 | Banks |
| 2010/0226863 A1 | 9/2010 | Piraino |
| 2010/0310654 A1 | 12/2010 | Jacono |
| 2010/0316737 A1 | 12/2010 | Farrington et al. |
| 2011/0038949 A1 | 2/2011 | Oswal et al. |
| 2012/0245084 A1* | 9/2012 | Carter .................. A61K 38/18 514/5.8 |

FOREIGN PATENT DOCUMENTS

| | | |
|---|---|---|
| FR | 2 592 790 | 7/1987 |
| FR | 2 924 611 | 6/2009 |
| WO | WO-94/04186 | 3/1994 |
| WO | WO-95/15761 | 6/1995 |
| WO | WO-2008/078331 | 7/2008 |
| WO | WO-2008/102368 | 8/2008 |
| WO | WO-2009/087424 | 7/2009 |
| WO | WO-2009/133573 | 11/2009 |

OTHER PUBLICATIONS

CPG Sec. 400.400 Conditions Under Which Homeopathic Drugs May be Marketed, Page Last Updated: Mar. 20, 2015, accessed online at https://www.fda.gov/ICECI/ComplianceManuals/CompliancePolicyGuidanceManual/ucm074360.htm, pp. 1-6. (Year: 2015).*

Benveniste, J., "Transfer of Biological Activity by Electromagnetic Fields," Frontier Perspectives vol. 3, No. 2, Fall 1993, pp. 13-15 (3 pp.).

British House of Commons Science and Technology Committee Report of 2009-2010, Feb. 22, 2010, p. 275 (1 p.).

Del Giudice, E. et al., "Water as a Free Electric Dipole Laser," Physical Review Letters, vol. 61, No. 9, Aug. 29, 1988, pp. 1085-1088 (4 pp.).

DesBio Product Catalog, Aug. 19, 2009 (155 pp.).

Ernst, Edzard, Homeopathy: What Does the "Best" Evidence Tell Us?, MJA, vol. 192, No. 8, Apr. 19, 2010, pp. 458-460 (3 pp.).

Field, J.B., Mechanism of Action, The Thyroid, $4^{th}$ edition, pp. 185-195, 1978 (13 pp.).

Fralish, G.B. et al., Consequences of Single-Chain Translation on the Structures of Two Chorionic Gonadotropin Yoked Analogs in {alpha}-{beta} and {beta}-{alpha} Configurations, Molecular Endocrinology 17: 757-767, Jan. 9, 2003 (12 pp.).

French Nobelist Escapes 'Intellectual Terror' to Pursue Radical Ideas in China, Science, vol. 330, p. 1732, Dec. 24, 2010 (1 p.).

Furuhashi, M. et al., Fusing the Carboxy-Terminal Peptide of the Chorionic Gonadotropin (CG) β-Subunit to the Common α-Subunit: Retention of O-Linked Glycosylation and Enhanced in Vivo Bioactivity of Chimeric Human CG, Molecular Endocrinology 9: 54-63, 1995 (10 pp.).

HPRS General Pharmacy, Dec. 2004 (16 pp.).

International Search Report and Written Opinion, International Patent Application No. PCT/US2012/030402, dated Jul. 4, 2012 (11 pp.).

International Search Report and Written Opinion, International Patent Application No. PCT/US2011/036513, dated Sep. 16, 2011 (11 pp.).

Kleijnen, J., et al., "Clinical Trials of Homoeopathy," Brit. Med. J. vol. 302, Feb. 9, 1991, pp. 316-323 (8 pp.).

Lapthorn, A.J. et al., Crystal Structure of Human Chorionic Gonadotropin, Nature, 369, Jun. 9, 1994 (2 pp.).

Lephart, E., Human Biology Review, pp. 41-42, 2009 (4 pp.).

Linde et al., Impact of Study Quality on Outcome in Placebo-Controlled Trials of Homeopathy, J. Clin. Epidemiology, vol. 52, No. 7, 1999, pp. 631-636 (6 pp.).

Linde et al., Are the Clinical Effect of Homeopathy Placebo Effects? A Meta-Analysis of Placebo-Controlled Trials, The Lancet, vol. 350, Sep. 20, 1997, pp. 834-843 (10 pp.).

Martius F. Das Arndt-Schultz Gnindgesetz, Edizinische Wochenschrift, Muench Med. Wschr., vol. 70, No. 31, Aug. 3, 1923, pp. 1005-1006 (2 pp.).

Montagnier, L. et al., Electromagnetic Signals Are Produced by Aqueous Nanostructures Derived from Bacterial DNA Sequences. Interdiscip Sci Comput Life Sci: 1:81-90, Jan. 6, 2009 (10 pp.).

Part 1—Endocrine Regulation of the Reproductive System in Reproduction Endocrinology, ed. Yen, SSC et al., Saunders Publishing Co., Philadelphia, PA, USA, pp. 34-62, 1987 (29 pp.).

Pierce, J.G. et al., Glycoprotein Hormones: Structure and Function, Ann Rev Biochem, 50: 465-495, 1981 (31 pp.).

Reilly, D., et al., "Is evidence for homoeopathy reproducible?", Lancet, vol. 344, Issue 8937, Dec. 10, 1994, pp. 1601-1608 (7 pp.).

Riley, D., et al., Clinical Homeopatic use of RNA: Evidence from Two Provings, Homeopathy, vol. 94, 2005, pp. 33-36 (4 pp.).

Sacks, A. D., "Nuclear Magnetic Resonance Spectroscopy of Homeopathic Remedies," Journal of Holistic Medicine, vol. 5, No. 2, Fall/Winter 1983, pp. 172-176 (5 pp.).

Shang et al., Are the Clinical Effects of Homeopathy Placebo Effects? Comparative Study of Placebo-Controlled Trials of Homeopathy and Allopathy, The Lancet, vol. 366, Aug. 27, 2005, pp. 726-732 (7 pp.).

Singh, L. M. et al. "Antiviral efficacy of homeopathic drugs against animal viruses," The British Homeopathic Journal, vol. 74, No. 3, Jul. 1985, pp. 168-174 (7 pp.).

Smith, R. B. et al., "Changes Caused by Succussion on NMR Patterns and Bioassay of Bradykinin Triacetate (BKTA) Succussions and Dilutions," Journal of the American Institute of Homeopathy, vol. 61, Oct.-Dec. 1968, pp. 197-212 (16 pp.).

Smith, R. B. et al., "Modern Instrumentation for the Evaluation of Homeopathic Drug Structure," Journal of the American Institute of Homeopathy, vol. 59, Sep.-Oct. 1966, pp. 263-279 (17 pp.).

Sugahara, T. et al., Biosynthesis of a biologically active single peptide chain containing the human common α and chorionic gonadotropin β subunits in tandem, Proc Natl Acad Sci: 92: 2041-2045, Mar. 1995 (5 pp.).

Taurox SB, ImmuneWellness.com, 2005 (1 p.).

U.S. Food and Drug Administration (FDA), Inspection, Compliance, Enforcement, and Criminal Investigations, CPG Sec. 400.400 Conditions Under Which Homeopathic Drugs May be Marketed, U.S. Department of Health & Human Services, Mar. 1995 (4 pp.).

U.S. Pat. No. 9,603,898, Mar. 28, 2017, U.S. Appl. No. 13/428,907, filed Mar. 23, 2012, Carter, et al., Formulations of Diluted Amino Acid Segments and Methods for Making Same.

US-2012/0071543, Mar. 22, 2012, U.S. Appl. No. 13/107,663, filed May 13, 2011, Carter, et al., Formulations fo Diluted Genetic Material and Methods for Making Same.

* cited by examiner

```
                        SEQUENCE LISTING

<160> NUMBER OF SEQ ID NOS: 2

<210> SEQ ID NO 1
<211> LENGTH: 25
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile
            20                  25

<210> SEQ ID NO 2
<211> LENGTH: 30
<212> TYPE: PRT
<213> ORGANISM: Homo sapiens

<400> SEQUENCE: 2

Gln Asp Ser Ser Ser Ser Lys Ala Pro Pro Pro Ser Leu Pro Ser Pro
1               5                   10                  15

Ser Arg Leu Pro Gly Pro Ser Asp Thr Pro Ile Leu Pro Gln
            20                  25                  30
```

FORMULATIONS OF DILUTED AMINO ACID SEGMENTS AND METHODS FOR MAKING SAME

CROSS-REFERENCE TO RELATED PATENT APPLICATIONS

This is a divisional of U.S. patent application Ser. No. 13/428,907, titled "Formulations of Diluted Amino Acid Segments and Methods for Making Same," filed on 23 Mar. 2012, issued as U.S. Pat. No. 9,603,898, which claims the benefit of U.S. Provisional Patent Application No. 61/466,638, titled "Homeopathic Formulations Using Naturally Occurring Amino Acid Segments as the Active Compound," filed on 23 Mar. 2011, all of which are incorporated by reference into this document in their entirety. In the event of a conflict, the subject matter explicitly recited or shown herein controls over any subject matter incorporated by reference. The incorporated subject matter should not be used to limit or narrow the scope of the explicitly recited or depicted subject matter.

MATERIAL SUBMITTED IN AN ELECTRONIC FORMAT AND INCORPORATED BY REFERENCE

The entire contents of the following electronic file submitted in an electronic format are incorporated by reference into this document:

TABLE 1

| File Name | Creation Date | Size in Bytes |
|---|---|---|
| Sequence ST25.txt | 17 Dec. 2013 | 903 |

BACKGROUND

Many Americans use complementary and alternative medicine (CAM) in pursuit of health and well-being. The 2007 National Health Interview Survey (NHIS), which included a comprehensive survey of CAM use by Americans, showed that approximately 38 percent of adults use CAM.

CAM is a group of diverse medical and health care systems, practices, and products that are not generally considered part of conventional medicine. Conventional medicine (also called Western or allopathic medicine) is medicine as practiced by holders of M.D. and D.O. degrees and by allied health professionals, such as physical therapists, psychologists, and registered nurses. The boundaries between CAM and conventional medicine are not absolute and specific CAM practices may, over time, become widely accepted.

The term "complementary medicine" refers to use of CAM together with conventional medicine. An example is the use of acupuncture along with conventional medicinal techniques to lessen pain. Most use of CAM by Americans is complementary. "Alternative medicine" refers to use of CAM in place of conventional medicine. "Integrative medicine" (also called integrated medicine) refers to a practice that combines both conventional and CAM treatments for which there is evidence of safety and effectiveness.

One type of CAM is the whole medical system of homeopathy. It is a complete system of theory and practice that has evolved over time in different cultures and apart from conventional medicine. Homeopathy is used for wellness and prevention and to treat many diseases and conditions.

Homeopathy dates back to the eighteenth century and is founded on the principles of pharmacology and biology. Homeopathy seeks to stimulate the body's ability to heal itself by giving very small doses of highly diluted substances. The therapeutic method that is the foundation of modern homeopathy was first developed by German physician Samuel Hahnemann. He articulated two of the foundational principles of homeopathy.

The first is the principle or law of similars (or "like cures like"). This principle states that a disease can be cured by a substance that produces similar symptoms in healthy people. Hahnemann theorized that if a substance could cause certain disease symptoms in a healthy person, then small amounts of the substance could cure a sick person who had similar symptoms.

The second is the principle of dilutions (or "law of minimum dose"). This principle states that the lower the dose of medication, the greater its effectiveness. Hahnemann theorized that the power of a given dose of medication is related to the surface area of molecules with which it comes into contact.

Later researchers further refined and developed the principles outlined by Hahnemann. In the late nineteenth century, Hugo Schultz postulated that the effect of a stimulus on a living cell is indirect and proportional to its intensity and quantity. Later, he demonstrated that very low concentrations of yeast toxins increased yeast growth over 100 fold.

At about the same time, the psychiatrist Rudolph Arndt developed his "Basic Law of Biology," which states that weak stimuli slightly accelerate the vital activity, middle-strong stimuli raise it, strong stimuli suppresses it, and very strong stimuli halt vital activity. These separate observations were formulated by Arndt into one of the earliest laws of pharmacology representing the homeopathic effect, the Arndt-Schultz law, which states: every stimulus on a living cell elicits an activity, which is inversely proportional to the intensity of the stimulus (Martius F. Das Arndt-Schultz Gnindgesetz, Muench Med. Wschr., 1923, 70(31):1005-1006).

One of the basic tenets of homeopathy is that a cure or treatment for a disease can be evoked by using a high dilution of a material that resembles but is different from the cause of the disease. Homeopathy is widely accepted as a useful therapeutic and has been demonstrated to have characteristic and reproducible effects. A critical review of more than 100 controlled and/or clinical studies of homeopathy determined that patients received positive healing benefits from homeopathy beyond the placebo effect (Kleijnen, J. et al. 1991 Brit. Med. J. 302:316-323; Linde, K., Clausius, N., Ramirez, G., Melchart, D., Eitel, F., Hedges, L. V., Jonas, W. B., 1997, Lancet, 350:834-843; Reilly, D., et al, 1994, Lancet, 344:1601-1608).

Many homeopathic remedies are used in very low concentrations on the order of micrograms ($10^{-6}$ M) and nanograms ($10^{-9}$ M); however, in other homeopathic preparations, the dilutions exceed Avogadro's number ($6.023 \times 10^{-23}$). When homeopathic compounds are repetitively diluted 1:10 (written as "X") or 1:100 (written as "C"), with repeated succussions (similar to vortexing) at least 24 times, a potency is achieved ($10^{-24}$ or 24X or 12C) that is so highly dilute that the probability of a single molecule of the original substance remaining in the volume used is less than $1 \times 10^{-10}$.

Homeopathic practitioners believe that the potency of a compound increases with increasing dilutions. In traditional homeopathic practice, the standard homeopathic dosage is 10-15 drops of a $10^{-12}$ molar, or 6C, solution administered two to three times per day. A $10^{-60}$ molar or 30C may be given one to three times per day. A $10^{-400}$ molar or 200C may be given only one time per month or year. A 6C dilution approximates 1 picogram/ml, which is used in cell culture but would be considered a lower than physiological dose when administered to a patient either orally, topically or by injection.

Highly dilute homeopathic remedies have been effective in treating some conditions, including viral infections, in vivo. Homeopathic dilutions of 200X to 1000X of typhoidinum, hydrophobinum, tuberculinum, nux vomica and malandrinum 100% inhibited pock-like lesions caused by a chicken embryo DNA virus on the chorio-allantoic membrane compared to controls (Singh, L. M. and Gupta, G. 1985 Brit. Homeopathy 74:168-174). Other homeopathic remedies, the same active compound at different homeopathic concentrations, or control phosphate buffered solution (PBS), had lesser or no effect.

While the exact mechanism of action of homeopathic remedies is unknown, magnetic resonance image measurements on serial dilutions of substances indicate that the hydroxyl (OH) groups in the solvent of solutions continue to change as dilutions become successively higher (Sacks, A. D. 1983 J. Holistic Med. 5:175-176; Smith, R. and Boericke, G. 1968 J. Am. Inst. Homeopathy 61:197-212; Smith, R. and Boericke, G. 1966 J. Am. Inst. Homeopathy 59:263-279). It is clear that the specific effects of homeopathics are of a non-molecular origin, yet provide potent biological activities that are clinically effective.

It has been postulated that highly dilute compounds transfer biological activity to cells by electromagnetic fields (Benveniste, J. 1993 Frontier Perspectives 3:13-15). Del Giudice et al. have hypothesized that interactions between the electric dipoles of water and the radiation fields of a charged molecule generate a permanent polarization of water which becomes coherent and has the ability to transmit specific information to cell receptors, somewhat like a laser (Del Giudice, E., Preparata, G., Vitiello, G. 1988, Phys. Rev. Lett. 61:1085-1088).

One common homeopathic formulation uses proteins, especially naturally occurring proteins, as the active compound. Although these formulations have largely been shown to be effective, they have come under increased scrutiny by government agencies responsible for the safety and security of food, cosmetics, dietary supplements, and the like. The agencies are concerned that formulations made using certain proteins may represent an unknown or ill defined risk to the end user.

It would be desirable to develop a homeopathic formulation that provides the same benefit of formulations prepared with complete proteins but with a lower risk profile.

SUMMARY

A number of representative embodiments are provided to illustrate the various features, characteristics, and advantages of the disclosed subject matter. The embodiments are provided in the context of preparing and administering diluted formulations to patients in order to increase wellness and overall health. It should be understood, however, that the individual concepts and features disclosed in connection with one embodiment can be used alone or in various combinations and sub-combinations with one another.

A highly diluted formulation and methods for making and using the same are disclosed herein. The formulation is prepared using one or more amino acid segments each of which includes a peptide sequence that is the same as a portion of a longer peptide sequence found in a naturally occurring material. The length of each peptide sequence can be at least 5 amino acids, at least 10 amino acids, at least 15 amino acids, or at least 20 amino acids.

In one embodiment, the amino acid segments are the same as the more biologically active regions of the peptide sequence found in the naturally occurring material. In other words, these peptide sequences are shown or believed to have a stronger association with a health effect in humans than the other peptide sequences.

For example, the amino acid segments may be associated with an increased susceptibility or resistance to a specific health condition or disease. The amino acid segments can also be associated with positive health effects such as weight loss, anti-aging, increased wellness, muscle development, athletic endurance, and fast twitch muscle response The amino acid segments can have a variety of peptide sequences. For example, the entire peptide sequence of the amino acid segment can be the same as a portion of a longer peptide sequence found in a naturally occurring material. In other words, the entire peptide sequence of the amino acid segment can be found in natural sources such as naturally occurring protein.

The amino acid segments can also include yoked amino acid chains or tandem amino acid repeats. The peptide sequences of these amino acid segments can be divided into separate portions which are the same as peptide sequences found in nature. For example, an amino acid segment may have a peptide sequence where one portion is the same as a terminal end of a naturally occurring peptide sequence of an alpha protein subunit and another portion is the same as a terminal end of a beta protein subunit. The amino acid segments may include one, two, three, four, or more of such portions.

The peptide sequence of the amino acid segments can include any combination (in any order) of individual peptide sequences that are the same as a portion of a longer peptide sequence found in nature. In one embodiment, the length of each individual peptide sequence is at least 5 amino acids, at least 10 amino acids, at least 15 amino acids, at least 20 amino acids, or at least 25 amino acids.

The amino acid segments can include any one or combination of peptide sequences from any suitable naturally occurring material, but preferably from naturally occurring materials that are believed to affect human health. In one embodiment, the amino acid segments include any one or combination of peptide sequences from a protein such as a glycoprotein or, specifically, a glycoprotein hormone. In another embodiment, the amino acid segments include one or more peptide sequences from a hormone such as a peptide hormone.

The amino acid segments can also include one or more peptide sequences from the following materials: human chorionic gonadotropin (hCG), follicle stimulating hormone (FSH), luteinizing hormone (LH), thyroid-stimulating hormone (TSH), human growth hormone (HGH), insulin, leptin, angiotensin, cholecystokinin (CCK), and ghrelin.

The amino acid segments can be synthesized or obtained directly from natural sources. The former is preferred because the amino acid segments can be readily and economically synthesized using conventional techniques. Direct extraction of the amino acid segments from natural sources may be suitable in some situations, but it is typically more difficult and less economical.

The diluted formulation is prepared by mixing one or more amino acid segments having the same or different peptide sequences and a diluting agent to form a mixture and then serially diluting at least a portion of the mixture. The mixture can also include amino acids that are not part of a naturally occurring peptide sequence. These may be present in the form of entire amino acid segments or portions of the segments for which there is no corresponding sequence found in natural sources. In general, however, it is desirable to minimize the number of non-naturally occurring peptide sequences.

The peptide sequence of the amino acid segments can include portions that are not: (1) at least five amino acids long and (2) the same as a portion of one or more longer peptide sequences found in a naturally occurring material. However, it is desirable that at least 50% (or at least 75%, at least 90%, or at least 95%) of the peptide sequence of the amino acid segments be at least five amino acids long (or any of the lengths described above) and the same as a portion of one or more longer peptide sequences found in one or more naturally occurring materials.

In one embodiment, at least 5% w/w (or 5% w/w to 100% w/w including any amount in between) of the amino acid segments in the mixture include peptide sequences of at least five amino acids that are the same as a portion of one or more longer peptide sequences found in one or more naturally occurring materials. In another embodiment, at least 5% w/w (or 5% w/w to 100% w/w including any amount in between) of the amino acid segments in the mixture include peptide sequences of at least five amino acids that are the same as a portion of one or more longer peptide sequences found in a single naturally occurring material.

The mixture can also include a variety of additional materials such as other biologically active compounds. For example, the mixture can include carbohydrate molecules that enhance the biological action of the amino acid segments when administered via standard oral homeopathic dosing.

The diluting agent in the mixture can be any suitable material that is suitable for oral ingestion. For example, the diluting agent can be water, ethanol, glycerin, lactose, and/or sucrose, among other materials. The first mixture is serially diluted to produce the final formulation. Each increasingly dilute mixture is succussed or vigorously shaken to potentize or activate it. In one embodiment, the final formulation is a homeopathic remedy.

Any suitable dilution ratio may be used to dilute the first mixture. The dilution ratio for each successive, increasingly dilute mixture may be the same or different. In one embodiment, the first mixture is diluted on a decimal or centesimal scale using the same dilution ratio for each step.

The increasingly dilute mixtures can be succussed in a number of different ways. At a minimum, the succussion process includes vigorous shaking. However, succussion can also include subjecting the mixtures to an impact force. It can also include vortexing the mixtures, which is a specific type of vigorous shaking. The mixtures can be succussed for any suitable length of time and with or without a pause between each vigorous shaking episode.

The final formulation can be provided in a variety of forms. Examples of common forms include liquid dilutions that are dispensed from a dropper, pellets, tablets, and capsules. Other forms include ointments, gels, and suppositories. The formulations may be sold over the counter or by prescription.

The final formulation can be used to naturally support and nurture the body's ability to overcome or manage undesirable health conditions and promote the body's ability to enhance desirable health effects. The formulation supports the body's own internal processes that are the source of many individual health effects.

In one embodiment, the formulation can be administered as a therapeutic agent for human health that promotes, prevents, treats, supports, and/or ameliorates: infertility, weight control, obesity, appetite control, diabetes, thyroid disease, hypertension or blood pressure control, anti-aging, and growth and development. It is especially useful when the health effect is mediated by glycoprotein or protein chemical messenger action, G-protein coupled receptor modulation with subsequent cyclic AMP generation and a cascade of intercellular enzymatic mechanisms involved in regulating signal transduction and hormone synthesis or conversion and/or the production of molecules influencing reproductive processes, metabolic and cardiovascular actions.

The formulation can influence, modulate, and/or support: metabolic hormone levels, metabolic hormone actions, chemical messenger-dependent reproductive molecules, cardiovascular function, and/or blood sugar control. The use of amino acid segments is an important intervention for the maintenance and improvement of human health, especially with aging and the prevention and treatment of various disorders.

Although the formulation is prepared primarily for use by humans, it should be appreciated that it may also be made to influence the health of animals. In the case of animals, the included amino acid segments are associated with one or more health effects in the species, or specific animal, for which the formulation is made. Formulations may be made for animals such as cats, dogs, horses, and so forth.

The term "v/v" means the volume fraction of a material (i.e., the volume of the specified material divided by the volume of the total solution). The term "w/w" means the weight fraction of a material (i.e., the weight of the specified material divided by the weight of the total solution). The two terms may be expressed as a percent by multiplying the value by 100.

The Summary is provided to introduce a selection of concepts in a simplified form that are further described below in the Detailed Description. The Summary and the Background are not intended to identify key concepts or essential aspects of the disclosed subject matter, nor should they be used to constrict or limit the scope of the claims. For example, the scope of the claims should not be limited based on whether the recited subject matter includes any or all aspects noted in the Summary and/or addresses any of the issues noted in the Background.

DETAILED DESCRIPTION

Formulation that include highly diluted amino acid segments can be prepared and administered to humans or animals to treat or otherwise address health effects that are influenced or affected by the amino acid segments. The formulation is created by mixing the amino acid segments with a diluting agent and serially diluting the resulting mixture. The final formulation can be a homeopathic remedy that is administered and dispensed in a similar way to other homeopathic remedies.

One or more amino acid segments are used as the source material to prepare the formulation. The amino acid segments are typically selected because they are associated with a health effect in the patient such as an increased susceptibility or resistance to an illness, disease, ailment, malady, or, on the other hand, a beneficial health characteristic such as weight loss, improved vision, anti-aging, metabolism speed, hair growth, and the like. The amino acid segments may be selected for other reasons beyond being associated with a health effect.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

In general, the one or more amino acid segments used in the formulation are selected because they represent the more biologically active region of a longer peptide sequence found in a naturally occurring material such as a protein or peptide hormone. A more detailed description of proteins and their functions follows.

Proteins are very important organic molecules which are widely distributed in plants, animals and humans. However, the way proteins are generated differs between plants and animals. Plants have the ability to synthesize all kinds of proteins, while animals and humans can only synthesize a limited number of proteins. Because of this, animals and humans rely on plants (and/or other animals) to fulfill their dietary need for protein.

The term protein was first introduced by G. J. Mulder in 1838. He discovered an organic material within cells which was basic to all organized bodies (or cells). Due to the importance of this substance he named it protein which originates from the Greek term protos, meaning first. Mulder was correct in assigning this substance a high level of importance because proteins account for about one-half of the total (dry weight) of plants and animals.

These "albuminoid substances" are so abundant and important that they stayed at the center of biological investigations and scientific debate throughout the 1900s. How proteins function within cells is essential to the development, maintenance, adaptability and survival of the individual.

Proteins are constructed based upon instructions that originate with DNA. This concept was first proposed by F. Crick in 1957 in a lecture given to the Society of Experimental Biologists entitled "On Protein Synthesis." Crick's sequence hypothesis can be summarized like this: DNA codes (like a message, by the order of its nucleotide sequence) the information to make messenger RNA.

The information is contained in the nucleotide sequence of the messenger RNA, which is processed using the biochemical machinery in cells to make proteins. There is a 3 to 1 correspondence between the messenger RNA nucleotides and an individual unit of a protein—i.e., an amino acid. In other words, it takes 3 messenger RNA nucleotides to produce a single amino acid. Thus, protein synthesis proceeds like this: DNA→encodes messenger RNA→encodes proteins. Proteins are composed of individual units, similar in nature to that of DNA and RNA.

Proteins are composed of individual units called amino acids. There are approximately twenty different amino acids that can be joined together by chemical bonds, called peptide bonds. Groups of amino acids bonded by peptides form a protein or polypeptide. This arrangement of the individual amino acids can be thought of like "beads on a string." The twenty different amino acids make up the protein alphabet and each amino acid would represent each individual bead of the string. The different combination of the individual amino acids and the way they are arranged in their linear sequence determines the characteristics of the particular protein subunit. There are different ways to classify proteins, but one basic concept is that a protein's structure, based upon its sequence of amino acids, will define its function.

It is estimated that the human body may contain over two million proteins, coded by only 20,000 to 25,000 genes, although more than 85% of the total protein within cells function as biological catalyst or enzymes. The term "enzyme" was introduced in 1876 (i.e., a protein catalyst increases the rate of a specific biochemical reaction). The importance of proteins became apparent when a hypothesis describing the "enzyme theory of life" was proposed.

Other examples of proteins include: storage proteins like, the ovalbumin in egg whites; myosin and actin in muscle fibers; casein as a milk protein; elastin fibers under the skin; collagen in bone, teeth and cartilage; fribrinogen and thrombin involved in blood clotting reactions; hemoglobin and myoglobin as oxygen-binding proteins; pepsin and trypsin as digestive enzymes; antibodies that function in the immune system; insulin and glucagons that regulate blood glucose levels; and antibiotics used to fight bacterial infections.

There are many more examples of proteins that could be presented, like structural proteins, which make up hair, nails, connective tissue, ligaments and tendons, or proteins that are involved in the repair of cells and tissues. Furthermore, there are many different types of proteins or amino acid segments within the bloodstream that serve as chemical messengers and/or within cells that serve both structural and metabolic functions.

The following is a description of glycoprotein structure and function. The term "glycoprotein hormone" usually is applied to gonadotropins from different tissue sites that are also glycosylated. There are two pituitary gonadotropins, luteinizing hormone (LH) (also known as, lutropin or intersitital cell-stimulating hormone) and follicle-stimulating hormone (FSH) or follitropin. Their general biological functions involve the stimulation of testicular and ovarian via cell-surface receptors for the regulation and production of gametogenesis and steroid hormone synthesis in gonadal tissues.

Pituitary thyroid-stimulating hormone (thyrotropin or TSH) regulates a wide variety of metabolic, biochemical and physiological processes resulting in the synthesis and secretion of thyroid hormones (T3 and T4). The most studied of the glycoproteins is human chorionic gonadotrophin (hCG).

The glycoproteins include two peptide or amino acid chains called subunits, designated alpha and beta. Both subunits are glycosylated at specific residues and are cross-linked internally by disulfide bonds. For example, the alpha subunit of hCG, FSH, and LH can have disulfide bonds between cysteine amino acid residues. These hormones are found in all mammals and within a species the alpha amino acid sequence or subunit is identical for each of the glycoprotein hormones while the beta subunit varies.

The distinguishing feature of hCG, FSH, LH and the thyrotropin hormone family is their heterodimeric structure, consisting of a common alpha subunit and a hormone-specific beta subunit. However, it has been proposed that the entire array of subunits initially evolved from a single gene. Although, crystal structure data suggests certain similarities between the common alpha subunit and the hCG beta subunit.

It is an assumed and accepted axiom that gonadotropin subunit assembly is vital to the function or biological activity of the hormone. For example, i) only dimers of the alpha and beta subunits are biologically active, ii) the confirmation of the heterodimer complex signals the addition of the hormone-specific oligosaccharides (or glycoside chain) that contribute to the circulatory half-life and to signal transduction of the chemical messenger, and iii) the secretion efficiency of the dimers is determined by the beta subunit.

The amino acid segments can include a portion or the entire common alpha subunit and hormone specific beta subunit as a single polypeptide chain to achieve a desired biological response. Instead of synthesizing the separate alpha and beta subunits that are found in vivo, single-chain analogs of the identical amino acids or smaller segments of the amino acids from both alpha and beta subunits can be synthesized and have a longer biological half-life activity.

Furthermore, the analog of the common alpha and specific hCG beta subunits synthesized as a single amino acid chain can fold into an appropriate conformation and the noncovalent linkage of the subunits is not required for biological activity. For example, an amino acid segment synthesized from the C-terminal end of the hCG beta subunit fused to the N-terminal end or amino acid sequence of the alpha subunit has biological activity similar to the endogenous or natural heterodimer.

Analogs alpha-beta and beta-alpha configuration for yoked hCG amino acids sequences along with three-dimensional conformations allow for binding to endogenous receptors via activation of G-protein-coupled function and stimulation of downstream cascade mechanisms (GB Fralish et al., 2003, Mole Endo, 17: 757-767).

Finally, glycosylation of a tandem or yoked C-terminal end of hCG containing the four serine-linked oligosaccharides with the N-terminal end of the alpha subunits displays increased biological activity. Thus, amino acid segments that include one or more peptide sequences that are the same as a portion of longer natural amino acid sequences may be constructed or synthesized from the alpha and the beta subunits of the glycoproteins to produce biologically active and high efficacy compounds.

Segments of naturally occurring amino acid sequences from the common alpha and specific beta subunits can be produced or synthesized in approximately 5, 10, 20, 30, 40 or 50 amino acid chains or more. The amino acid segments can be single independent sequences from a subunit, tandem or yoked segments having different subunit sequences, or combinations of amino acid mixtures.

The amino acid segments can be derived from glycoproteins, such as those mentioned above, and other proteins that do not have a and is subunits. Examples of other proteins include human growth hormone (HGH) for development, growth and improvement of general health, insulin for regulation of blood sugar levels and diabetes, angiotensin II for the modulation of blood pressure, leptin and ghrelin for weight control, and cholecystokinin (CCK) for appetite control.

In one embodiment, the amino acid segments are synthesized segments of naturally occurring amino acid sequences in proteins that have the common alpha and specific beta subunit structure (commonly found in glycoproteins). These segments can include approximately 5, 10, 20, 30, 40, or 50 amino acid chains that are independent from each other, tandem/yoked using different subunits, or combinations of these. The administered amino acid segments may also include amino acid segments of proteins that do not have alpha and beta subunit structures, such as HGH, insulin, angiotensin II, leptin, CCK, and ghrelin.

Table 1 below shows some examples of independent amino acid segments, tandem/yoked using different subunit amino acid sequences, or combinations of amino acid mixtures and their dosing range. The mixture may include any single amino acid segment or combination of amino acid segments shown in Table 1. For example, the mixture may include components A and B, a tandem AB amino acid segment, only E, or other combinations. Exemplary homeopathic dosing amounts per day are also shown in Table 1.

TABLE 2

Examples of Independent Amino Acid Segments, tandem/yoked using different subunit amino acid segments, or combinations of amino acid mixtures and dosing range.

| Component | Levels/Concentration Range of Dosing Per Day (Range by X Scale) | | |
|---|---|---|---|
| | #1 | #2 | #3 |
| A. Alpha (α) subunit 10, 20, 30, 40 or 50 amino acid sequence/segments of the N-terminal portion of the subunit | 1X to 6X | 2X to 12X | 8X to 400X |
| B. Human Chorionic Gonadotropin (hCG) 10, 20, 30, 40 or 50 amino acid sequence/segments of the C-terminal portion of the beta subunit | | | |
| C. Follicle Stimulating Hormone (FSH) 10, 20, 30, 40 or 50 amino acid sequence/segments of the C-terminal portion of the beta subunit | | | |
| D. luteinizing hormone (LH) 10, 20, 30, 40 or 50 amino acid sequence/segments of the C-terminal portion of the beta subunit | | | |
| E. Human Growth Hormone (HGH) 10, 20, 30, 40 or 50 amino acid sequence/segments of the peptide | | | |
| F. Insulin 10, 20, 30, 40 or 50 amino acid sequence/segments of the peptide | | | |
| G. Angiotensin II 5, 10 amino acid sequence/segments of the peptide | | | |
| H. Leptin 10, 20, 30, 40 or 50 amino acid sequence/segments of the peptide | | | |
| I. Cholecystokinin (CCK) 10, 20, 30, 40 or 50 amino acid sequence/segments of the peptide | | | |
| J. Ghrelin 10, 20, 30, 40 or 50 amino acid sequence/segments of the peptide | | | |

*It should be appreciated that the amino acid segments may be used at any of the dilution levels disclosed herein and not just those shown in the table. The dilution levels are provided in the table as examples of suitable dilution levels and should not be viewed as limiting in any way.

The amino acid sequences or segments may be synthesized using well known methods and techniques that are suitable for small or large scale production of high purity material. Examples of suitable methods include early methods such as the Strecker amino acid synthesis protocol and more recent technology involving automated sequencing techniques and improvements to established methodologies.

As mentioned above, the amino acid segments include a peptide sequence that is the same as a portion of a longer peptide sequence found in a naturally occurring material. The length of the peptide sequence in the amino acid segments can be at least 5 amino acids, at least 10 amino acids, at least 15 amino acids, at least 20 amino acids, or at least 25 amino acids.

The highly diluted formulation can be made using the amino acid segments as follows. The process includes preparing a first mixture (also referred to herein as the initial mixture or mother tincture) that includes the amino acid segments, diluting the first mixture with a diluting agent, and potentizing or activating the first mixture by vigorously shaking it. The dilution and shaking steps are repeated multiple times until the desired potency is reached.

The first mixture is prepared by mixing the amino acid segments with a diluting agent. The diluting agent can be any suitable material such as ethanol, water, glycerin, or any combination of these materials. The diluting agent preferably includes ethanol since it typically forms a more stable solution that keeps for a longer time. Aqueous or other types of solutions may be preferable in situations where the amino acid segments are soluble in water but not ethanol or the amino acid segments are subject to chemical change or decomposition in ethanol.

In one embodiment, the diluting agent includes at least approximately 20% v/v ethanol, at least approximately 60% v/v ethanol, at least approximately 70% v/v ethanol, or at least approximately 90% v/v ethanol. The remainder of the diluting agent can be water, and preferably distilled water. In another embodiment, the diluting agent includes no more than approximately 10% v/v water, no more than approximately 30% v/v water, no more than approximately 40% v/v water, or no more than approximately 80% v/v water.

The first mixture can include any suitable quantity and type of amino acid segments. It should be appreciated that if the amino acid segments are provided as part of a solution, any non-amino acid segments in the solution should be accounted for when determining the concentration of the amino acid segments in the first mixture. For example, if the amino acid segments are part of an aqueous solution that is combined with the diluting agent to form the first mixture, the water in the aqueous solution should be accounted for when determining the concentration of the first mixture.

In one embodiment, the first mixture includes no more than approximately $1/5$ w/w or v/v amino acid segments or no more than approximately $1/8$ w/w or v/v amino acid segments. In another embodiment, the first mixture includes at least $1/1000$ w/w or v/v amino acid segments or at least $1/500$ w/w or v/v amino acid segments. In yet another embodiment, the first mixture includes approximately $1/5$ w/w or v/v amino acid segments to approximately $1/1000$ w/w or v/v amino acid segments or approximately $1/8$ w/w or v/v amino acid segments to approximately $1/500$ w/w or v/v amino acid segments. Preferably, the first mixture includes approximately $1/10$ w/w or v/v amino acid segments or $1/100$ w/w or v/v amino acid segments.

In another embodiment, the peptide sequences of at least 5% w/w (or any 5% w/w increment from 5% w/w to 100% w/w) of the amino acid segments in the mixture are the same as a portion of one or more longer peptide sequences found in one or more naturally occurring materials. Desirably, at least 90% w/w (or 93% w/w, 97% w/w, or 99% w/w) of the amino acid segments in the first mixture are the same as a portion of one or more longer peptide sequence found in one or more naturally occurring materials.

In another embodiment, the peptide sequences of at least 5% w/w (or any 5% w/w increment from 5% w/w to 100% w/w) of the amino acid segments in the mixture are the same as a portion of one or more longer peptide sequences found in a single naturally occurring material such as a peptide hormone or protein. Desirably, at least 90% w/w (or 93% w/w, 97% w/w, or 99% w/w) of the amino acid segments in the first mixture are the same as a portion of one or more longer peptide sequence found in single naturally occurring material such as a peptide hormone or protein.

In some situations, it may be desirable to subject the amino acid segments to a maceration process before combining it with the diluting agent to form the first mixture. The maceration process proceeds as follows. The amino acid segments are placed in a container such as a jar or bottle and a solvent is added until it completely engulfs the amino acid segments. The container is closed, placed in a dark room at room temperature and vigorously shaken at regular intervals. This is done for up to two months and then the liquid in the container is decanted.

In other situations, it may be desirable to subject the amino acid segments to a percolation process before combining it with the diluting agent to form the first mixture. The percolation process proceeds as follows. The amino acid segments are dried and reduced to a fine powder. A solvent is mixed with the powder until it is uniformly and distinctly damp. The damp powder is transferred to a percolator, allowed to stand for one hour, and then packed firmly into the percolator.

The percolator should be provided with a stop-cock or other device to control the flow through the unit. A plug of absorbent cotton is inserted into the neck above the stop-cock and covered with a filter material. The damp powder is spread onto the filter material and then the filter material and plug are pressed down with a broad, inert tamper. Another piece of filter material is placed on top of the existing filter material.

While holding the filter and plug combination down, the solvent is poured upon the contents of the percolator until the filter and plug combination is covered, allowing the fluid to run gently down the rod so that the filter material is not displaced. Close the percolator to prevent evaporation. Close the valve or stop-cock as soon as the fluid begins to drop and allow it to stand 24 hours or longer depending on the nature of the contents. The fluid should pass through the percolator into the receiver, drop by drop, at a rate of approximately 10 to 30 drops per minute. Additional solvent should be periodically added to keep the liquid surface above the powder, thereby preventing access of air.

The amino acid segments may also be heated as part of the maceration or percolation processes or as part of another different process. The heat may cause the constituents of the amino acid segments to break down and lead to a more complex extraction of medicinal properties. The amino acid segments may be heated using any of a number of suitable techniques.

In one embodiment, the amino acid segments are incubated using the following process. The process is the same as that described for maceration above except that after the container is closed, it is heated up to 100° C. or up to 50° C. (e.g., approximately 37° C.) and maintained at the desired temperature, with occasional agitation, for approximately one hour. After cooling, the container is placed in a dark room and the maceration process proceeds as described above.

In another embodiment, the amino acid segments are heated using an infusion process. The dried amino acid segments and a solvent are placed in a container and allowed to stand for up to an hour (e.g., approximately 15 minutes). Boiling water is poured over the preparation and, under a reflux condenser, the contents are maintained at the boiling point for up to 30 minutes (e.g., approximately 5 minutes). The container is cooled to room temperature, closed, placed in a dark room at normal temperature, and vigorously shaken at regular intervals. The remainder of the process is similar to that described for maceration above.

In another embodiment, the amino acid segments are heated using a decoction process. The dried amino acid segments and a solvent are placed in a container and allowed to stand overnight. The contents are then heated under a reflux condenser and the boiling point is maintained for 30 minutes. After cooling, the container should be handled in the manner described for the infusion process.

The solvent mentioned above in connection with the maceration and percolation processes as well as the heating methods can be any suitable solvent. In one embodiment, the solvent can be the same as any of the diluting agents described above. Also, it should be appreciated that any of the heating methods described above can be used separately from the maceration or percolation processes. They can be used in conjunction with any other process or as a standalone heating step.

There may be some situations where the amino acid segments are not soluble in the diluting agent. In these situations, the amino acid segments can be converted into a form that can be introduced into the core process. This is done by diluting the amino acid segments while it is in a solid or semi-solid form using a process called trituration. The amino acid segments are combined with a solid diluting agent to form a first solid mixture. The solid diluting agent can be any suitable material such as lactose or sucrose. Preferably, the solid diluting agent is largely or entirely lactose.

The amino acid segments and the solid diluting agent are mixed together in any suitable way using any suitable equipment. In one embodiment, the materials are processed by hand using a mortar and pestle. This method may be especially useful when processing smaller quantities. In another embodiment, the materials are processed using mechanical equipment such as a ball mill. This device includes a cylindrical porcelain jar fitted with a tight lid. The materials are placed in the jar together with very hard porcelain cylinders. The jar is closed, placed on horizontal rollers, and rotated by electric motors for a long enough time to ensure complete and thorough mixing of the materials (e.g., approximately two hours). This method may be especially useful when processing larger quantities.

The first solid mixture can include any suitable amount and type of amino acid segments. In one embodiment, the solid mixture can have the same amount and types of amino acid segments as the first mixture described above.

The first solid mixture can be diluted further using the same process. The dilution ratio used for each successive, increasingly dilute solid mixture is preferably the same as the dilution ratio used to prepare the first solid mixture. However, the dilution ratio does not need to be the same and can potentially vary for each successive, increasingly dilute solid mixture.

Examples of suitable dilution ratios include 1:5 (it should be noted that this ratio is used by other dilution treatment methodologies but is not a proper dilution ratio in homeopathy), 1:10, 1:100, 1:1,000, 1:50,000, 1:100,000, 1:500,000, 1:1,000,000 or any ratio in between these. Since the materials are solid, the dilution ratio is preferably determined on a w/w basis. However, a w/v or v/v basis may be used as well to the extent practicable. The amount of amino acid segments in the increasingly dilute solid mixtures can be determined based on the original amount of amino acid segments in the first solid mixture, the number of times it was subsequently diluted, and the dilution ratio used each time.

One example of a trituration process is as follows. The first solid mixture is prepared by mixing the amino acid segments and the solid diluting agent at a ratio of 1:10 to form a mixture having a potency of 1X. It is mixed using a ball mill for two hours. The first solid mixture is diluted by mixing it with the solid diluting agent at a ratio of 1:10 and processed in a ball mill to produce a second solid mixture having a potency of 2X. The second solid mixture is then diluted further by mixing it with the solid diluting agent at a ratio of 1:10 and processed in a ball mill to produce a third solid mixture having a potency of 3X. The subsequent, increasingly dilute mixtures are all prepared using a dilution ratio of 1:10 to produce increasingly potent mixtures.

After one or more triturations, the solid mixture can be incorporated into the core process and used to prepare the first mixture referenced above. For example, the 3X trituration prepared above can be substituted for the amino acid segments used to prepare the first mixture. The 3X trituration readily dissolves in the diluting agent (e.g., ethanol, water, glycerin, etc.) and further dilution can proceed in the manner described below.

The first mixture is serially diluted to produce successive, increasingly dilute mixtures. The first mixture can be serially diluted any number of times using any suitable dilution ratio. The dilution ratio used to prepare each increasingly dilute mixture is preferably the same as the dilution ratio used to prepare the first mixture. However, the dilution ratio does not need to be the same and can potentially vary for each increasingly dilute mixture.

Examples of suitable dilution ratios include 1:5 (see previous note about this dilution ratio and its applicability to homeopathy), 1:10, 1:100, 1:1,000, 1:50,000, 1:100,000, 1:500,000, 1:1,000,000 or any ratio in between these. The dilution ratios may be on a w/w, w/v, or v/v basis. In one embodiment, the first mixture is diluted according to the decimal (X), centesimal (C), or fifty millesimal (LM) scale.

The final formulation may be labeled with a number followed by a roman numeral to indicate the final dilution and the manner in which the first mixture is serially diluted. Examples of such a label include 20X, 40C, and 20LM. The letter designation denotes the dilution ratio used in the process and the number before the letter indicates how many times the starting material has been diluted at that ratio. For example, V, X, C, and LM mean that each increasingly dilute mixture is prepared using a 1:5, 1:10, 1:100, and 1:50000 dilution ratio, respectively. The concentration can be determined by the number of dilutions given at the specified dilution ratio.

For example, a formulation labeled 40X has a concentration of $1 \times 10^{-40}$ and a formulation labeled 20C has the same concentration $1 \times 100^{-20}$ or $1 \times 10^{-40}$. Although the final concentration is the same, the formulations are not the same because the 40X formulation is prepared by undergoing 40 separate dilutions at a 1:10 dilution ratio and the 20C formulation is prepared by undergoing 20 separate dilutions at a 1:100 dilution ratio.

The designation M is also used as a potency designation on labels. However, the M is not a separate dilution ratio (like X, C and LM). It is merely shorthand for 1000C. The further dilution of a 1M potency includes serial 1:100 dilutions until the 2000th potency is reach, which is designated 2M. Thus, 10M means 10000C, 15M means 15000C, and so forth.

In one embodiment, the first mixture is serially diluted using an average dilution ratio of no more than approximately 1:5 or 1:10. It should be appreciated that the phrase "no more than" is used in the context of the decimal value of the dilution ratio and not the roman numeral notation used to refer to the dilution scale. For example, the decimal value of 1:5 is 0.2. The decimal value of the average dilution ratio is no more than approximately 0.2 but may be less than approximately 0.2 such as 1:10 (0.1) or 1:100 (0.01). Although the roman numeral notation increases as the decimal value of the dilution ratio drops, the decimal value is being referenced unless noted otherwise.

In another embodiment, the first mixture is serially diluted using an average dilution ratio of approximately 1:5 to approximately 1:1000000, approximately 1:10 to approximately 1:50000, or approximately 1:10 to approximately 1:100. The average dilution ratio refers to the average of all the dilution ratios used to serially dilute the first mixture. In situations where the same dilution ratio is used for each serial dilution, the average dilution ratio is the same as the dilution ratio used.

In another embodiment, the dilution ratio for each serial dilution of the first mixture is no more than approximately 1:5 or 1:10. In yet another embodiment, the dilution ratio for each serial dilution of the first mixture is approximately 1:5 to approximately 1:1000000, approximately 1:10 to approximately 1:50000, or approximately 1:10 to approximately 1:1000.

The diluting agent used to prepare each increasingly dilute mixture may the same as or different than the diluting agent used to prepare the first mixture. In one embodiment, the final formulation may be in the form of a solid tablet, pellet, or the like. The diluting agent includes at least approximately 50% w/w or v/v ethanol or at least approximately 70% w/w or v/v ethanol. In another embodiment, the final formulation is a liquid that is administered orally. The diluting agent used to dilute the first mixture and prepare a second mixture includes at least approximately 50% w/w or v/v ethanol or at least approximately 60% w/w or v/v ethanol. The diluting agent used to prepare the remainder of the increasingly dilute mixtures includes at least approximately 10% w/w or v/v ethanol or at least approximately 20% w/w or v/v ethanol.

The first mixture can be diluted using any suitable method. Two methods that can be used are the Hahnemannian and Korsakovian methods. The difference between the methods centers on whether the container is changed each time the mixture is diluted. The container is changed each time in the Hahnemannian method but is not in the Korsakovian method.

For example, a 3C formulation is made using the Hahnemannian method as follows. The 1C formulation is prepared by removing 1 part of the first mixture from its container and adding it to 99 parts of diluting agent in another container. The 2C formulation is prepared by removing 1 part of the 1C formulation from its container and adding it to 99 parts of diluting agent in yet another container. The 3C formulation is prepared by removing 1 part of the 2C formulation from its container and addition it to 99 parts of diluting agent in yet another container.

In contrast, a 3C formulation is made using the Korsakovian method in the same container. The 1C formulation is prepared by emptying the contents of the first mixture from the container so that 1 part remains (e.g., the small amount left on the walls and bottom of the container when it is emptied) and adding 99 parts diluting agent to the container. The 2C formulation is prepared by emptying the contents of the 1C formulation from the container so that 1 part remains and adding 99 parts diluting agent. This process is repeated again to produce the 3C formulation. In Korsakovian method every subsequent dilution is achieved by emptying the container of 99% on a w/w or v/v basis of the previous formulation and refilling it with fresh diluting agent.

An H or a K can be added to the label to indicate which method was used to produce the formulation. For example, 3CH indicates centesimal attenuation, Hahnemannian style. 3CK indicates centesimal attenuation, Korsakovian style.

A formulation can be prepared using the same method throughout or by combining the two methods or any other suitable method. In one embodiment, the Hahnemannian method is used for the first 12 to 200 serial dilutions and the Korsakovian method is used for additional dilutions. In another embodiment, the Hahnemannian method is used to prepare formulations up to 200C and the Korsakovian method is used to prepare formulations above 200C. For formulations above 200C, the Korsakovian method may be used for all of the serial dilutions or the Hahnemannian method may be used for each serial dilution up to 200C and then the Korsakovian method used thereafter.

Each successive, increasingly dilute mixture is potentized or activated by vigorously shaking the container holding the mixture. This vigorous shaking is known as succussion. Substances that are diluted without being vigorously shaken do not have the same wellness enhancing properties as succussed substances. Vigorously shaking the solution allows the formulation to remain potent past the point where none of the original molecules of amino acid segments remain in the dilution. The purely chemical effect of the amino acid segments are lost as it is diluted more and more, but with vigorous shaking the homeopathic effects are released. With vigorous shaking, the homeopathic remedy gets stronger and longer lasting with each successive dilution.

In one embodiment, each increasingly dilute mixture is succussed by subjecting it to vigorous shaking and an impact force. If the mixture is succussed by hand, this can be done by striking the container against an object such as a large book. If the mixture is succussed in an automated fashion, this can be done by a special mechanical shaking device. The device shakes the container and subjects it to an impact force.

In one embodiment, each increasingly dilute mixture is subjected to at least approximately 2 impact forces, at least approximately 5 impact forces, or at least approximately 10 impact forces. In another embodiment, each increasingly dilute mixture is subjected to approximately 2 to approximately 1000 impact forces, approximately 5 to approximately 100 impact forces, approximately 10 to approximately 50 impact forces, or approximately 20 to approximately 40 impact forces. The increasingly dilute mixtures may each be subjected to same number of impact forces or a different number of impact forces.

Each increasingly dilute mixture may be vigorously shaken for any amount of time that is desirable. In one embodiment, each increasingly dilute mixture is shaken for at least approximately 2 seconds, at least approximately 4 seconds, or at least approximately 8 seconds. In another embodiment, each increasingly dilute mixture is vigorously shaken for no more than approximately 2 hours, no more than approximately 1 hour, or no more than approximately 30 minutes. In yet another embodiment, each increasingly dilute mixture is vigorously shaken for approximately 2 seconds to approximately 2 hours, approximately 4 seconds to approximately 1 hour, or approximately 8 seconds to approximately 30 minutes. The increasingly dilute mixtures may each be vigorously shaken for the same amount of time or a different amount of time.

Each increasingly dilute mixture may be succussed by repeatedly starting and stopping the shaking. In one embodiment, each mixture is vigorously shaken at least approximately 2 times, at least approximately 5 times, or at least approximately 8 times. In another embodiment, each mixture is vigorously shaken no more than approximately 1000 times, no more than approximately 500 times, or no more than approximately 100 times. In yet another embodiment, each mixture is vigorously shaken approximately 2 to approximately 1000 times, approximately 5 to approximately 500 times, or approximately 8 to approximately 100 times.

It may be desirable to pause between shaking successive mixtures. In one embodiment, there is at least 1 minute, at least 2 minutes, or at least 3 minutes between shaking of each successive mixture. It should be appreciated that the pause between shaking successive mixtures may be any suitable length of time.

Formulations prepared using higher dilution ratios may require multiple dilutions between shaking. For example, a formulation can be prepared using the 1:50000 dilution ratio as follows. The amino acid segments are added as part of a liquid or a solid to lactose in a proportion of 1:100. If liquid, the amino acid segments are added using a dropper or other dispenser to the lactose. The mixture is then triturated to the 3C trituration in the manner described above. A portion of the trituration, e.g., 0.062 g, is added to 500 drops of diluting agent in a container. One drop of the resulting mixture is then added to 2 ml of diluting agent. The mixture is then shaken for the first time to form the 1LM formulation.

The 2LM formulation is prepared by mixing one drop of the 1LM mixture with 0.575 g #10 pellets (500 #10 pellets) to form medicated pellets. One of the medicated pellets is added to 2 ml of diluting agent. The mixture is shaken to form the 2LM formulation. This process is repeated until the desired dilution level has been achieved.

The final formulation can have any suitable concentration of the first mixture or the amino acid segments. In one embodiment, the concentration of either the first mixture or the amino acid segments in the final formulation is no more than approximately $1\times10-3$ on a w/w or v/v basis, no more than approximately $1\times10-4$ on a w/w or v/v basis, no more than approximately $1\times10-5$ on a w/w or v/v basis, or no more than approximately $1\times10-6$ on a w/w or v/v basis.

The potency of the final formulation is different than its concentration. In homeopathy, the potency increases as it becomes increasingly dilute. A formulation having a higher concentration of amino acid segments has a lower potency than one that's more diluted. The potency of the formulation is given by the label. For example, a 15X formulation is more dilute and, therefore, has a higher potency than a 10X formulation. Likewise, a 10C formulation has a higher potency than a 15X formulation (10C=20X). The potency of the final formulation is at least 1V, 1X, or, desirably, 2X.

The final formulation may have any potency referenced herein. In one embodiment, different potency chords can be prepared from the first mixture. For example, the first mixture can be used to create potencies of 3X, 6X, 12X, 100X, 200X, etc. These are referred to as potency or dilution chords because the different potencies are made from the same starting mixture. Any desirable potency chords can be prepared using any suitable dilution ratio or scale. In one embodiment, potency chords may be prepared The final formulation can be orally ingested by the patient in the form of a liquid, pellet or globule, or tablet. The liquid form can be packaged in any suitable container such as an amber glass bottle. It may also be dispensed from the container in any suitable manner such as with a dropper. The container can be any suitable size but preferably includes approximately 10 ml to approximately 100 ml of the final formulation or approximately 15 ml to approximately 60 ml of the final formulation. In another embodiment, the container includes approximately 10 ml, approximately 15 ml, approximately 30 ml, or approximately 60 ml of the final formulation.

The liquid form typically includes a mixture of purified water and ethanol, although it can include any combination of diluting agent and/or amino acid segments. The ethanol may be included to preserve the formulation and protect it from decomposition. In one embodiment, the final formulation includes no more than approximately 90% w/w or v/v ethanol, no more than approximately 75% w/w or v/v ethanol, no more than approximately 50% w/w of v/v ethanol, or no more than approximately 30% w/w or v/v ethanol. In another embodiment, the final formulation includes approximately 20% w/w or v/v ethanol, approximately 10% w/w or v/v ethanol, or approximately 5% w/w or v/v to approximately 25% w/w or v/v ethanol.

The pellet form is popular because it is easy to store and dispense. The diluting agent that makes up most of the pellet is sucrose, lactose, and/or other suitable polysaccharides. The pellets can be any suitable size and shape. In one embodiment, the pellets have a spherical shape and the size is designated according to the diameter of 10 pellets measured in millimeters. Standard sizes include very small pellets (#10), small pellets (#20), regular pellets (#35), and large pellets (#55). Pellets made of lactose will absorb alcoholic dilutions having a much larger percentage of water than will those made of sucrose.

The pellets may be medicated in any suitable way. In one embodiment, the pellets are medicated by placing them in a container and adding the last liquid formulation in a proportion of not less than 1% v/w (i.e., 1 drop of liquid for 2 g of unmedicated pellet). The pellets are allowed to soak for 3-5 minutes and then shaken to obtain the final formulation. The medicated pellets are dried at a temperature that is no more than approximately 40° C. This method may be especially suitable for situations where the liquid includes ethanol. If sucrose pellets are medicated then the liquid mixture should includes at least 70% w/w or v/v ethanol to prevent it from dissolving.

The pellets can be ingested sublingually (under the tongue) and allowed to dissolve for optimal absorption and utilization. They should be taken when there aren't other substances in the patient's mouth such as food, residues of tooth paste, mouth wash, gum, or the like. If the patient has recently eaten or had something in his or her mouth, then it may be desirable to have the patient wait approximately 1 hour before taking any pellets.

The tablet form can also be used to deliver the final formulation to the patient. Tablets differ from pellets based on how they are made and, in many situations, what they look like. The tablets can be made using any suitable process, although they are usually made using a different process than that used to make the pellets. Also, although the tablets and pellets may have any suitable shape, the pellets typically have a spherical shape and tablets have a non-spherical shape. Two examples of suitable tables include tablet triturates and compressed tablets.

Tablet triturates are soft, molded tablets produced from moist material on a triturate mold which gives them the shape of cut sections of a cylinder. They dissolve immediately when put in the patient's mouth. Tablet triturates are typically made using the following four step process. However, it should be appreciated that this process can be modified in a number of different ways and still produce a tablet that qualifies as a tablet triturate.

The first step in the method is to prepare a triturate having the desired potency in the manner described above. The second step is to add binder material to the mixture in any suitable amount (e.g., approximately 0.5 to approximately 2 parts binder to approximately 10 to approximately 20 parts triturate). The binder material may include any suitable material. In one embodiment, the binder material is provided as a solution that includes a binder (e.g., such as gum arabic or microcrystalline cellulose), an optional preservative, an inert lubricant, and purified water. The third step is to mold the tablets by hand or with suitable equipment. The fourth step is to dry the molded tablets at a temperature of 70° F. to 110° F.

Compressed tablets are hard tablets that do not dissolve immediately when put in the patient's mouth. These are typically meant to be swallowed with water because they take too long to dissolve orally. Compressed tablets are formed by preparing a triturate having the desired potency in the manner described above. A binder material that is similar to or the same as that described in connection with the tablet triturates can be added to the triturate. The mixture is then compressed to form a hard tablet that is similar to conventional medicine tablets.

The final formulation can also be administered in the form of a capsule. The final formulation may be a liquid or a solid (e.g., a powder) that is enclosed in the capsule and orally administered to the patient. The capsule dissolves in the patient's stomach and releases the final formulation.

In addition to liquids, pellets, tablets, and capsules, the final formulation may also be provided in the form of ointments, lotions, and gels, which can be applied externally. These typically have less therapeutic effect than internally consumed remedies. The final formulation can also be provided as a suppository.

In one embodiment, the final formulation is part of a homeopathic remedy. The final formulation is provided in any of the forms discussed above and packaged in any suitable container. A label is attached to the container that communicates to the user that the formulation inside is homeopathic in nature and/or includes amino acid segments of some potency such as at least 1X, at least 3X, and so forth.

It should be appreciated that the label does not need to use the words "amino acid segments" to communicate that amino acid segments are included in the formulation. Rather, the label can use a number of terms and descriptions to communicate this to the user. For example, the label may state that it includes one or more specific materials that qualify as amino acid segments. There are numerous other ways the label can communicate this to the user.

The concepts described herein may also be applied to imprinting or digital homeopathy. The underlying concept is that vibrational exchange is the language of biochemistry. Molecules produced by the body that govern physiology and molecules administered as a therapeutic treatment work by transmitting an electromagnetic signal or signature, vibrating at a specific frequency, termed the "resonance frequency," that can be sensed and responded to by the cells in the body. Therapeutic treatments work by getting close enough to the cell so that their resonance frequencies can be picked up and responded to.

It follows, then, that it may not be necessary to administer a physical substance to the patient. The patient can be directly influenced through application of the resonance frequency. Instead of administering the actual substance, its resonance frequency is determined and applied to the patient in a concentrated, or potentiated, form.

The physics by which serial dilution concentrates frequencies is difficult to understand. Suffice it to say that removing a molecule from solution that once emitted a frequency creates an entity called a hyperproton, which is basically concentrated energy. The frequency given off from a given therapeutic agent can be recorded, digitized, emitted or imprinted into a liquid medium and then given to a biological system to generate a biological effect—the same effect that would occur if the original molecule was administered in intact form.

The resonance frequency of the amino acid segments can be identified and used for imprinting purposes. In one embodiment, the resonance frequencies for various amino acid segments and/or final formulations are stored in a computer database. The frequencies can be transmitted into the patient's body via any suitable transmission system for the purpose of evaluating which frequencies are the most valuable or beneficial to the patient's body. The specific frequencies that your body finds of value can then be imprinted into a carrier solution. The patient then places one or more drops of the imprinted solution under his/her tongue. The specific frequencies enter the patient's body, distribute through the patient's energetic nervous system, and stimulate the patient's cells to respond. Alternatively, the specific frequencies may be applied directly to the patient.

It should be appreciated that any source of electromagnetic energy can be used to identify the resonance frequency of the amino acid segments and/or final formulations, imprint the carrier solution, or directly treat the patient. Examples of suitable sources of electromagnetic energy include RF, lasers, and the like.

In one embodiment, the final formulation can be used as part of a therapeutic treatment that includes measuring the electromagnetic signals of the amino acid segments in the formulation. For example, a homeopathic practitioner may measure a patient's energy field and then match that to the electromagnetic signature of a specific formulation to arrive at the appropriate treatment.

In another embodiment, the final formulation may be used as part of a therapeutic treatment such as that described in U.S. Pat. No. 6,142,927, titled "Method and Apparatus for Treatment with Resonant Signals," issued on 7 Nov. 2000, which is hereby incorporated by reference in its entirety. Specifically, the final formulation may be used to provide digital sequences that are stored in the computer as disclosed in the '927 patent.

EXAMPLES

The following examples are provided to further illustrate the disclosed subject matter. They should not be used to constrict or limit the scope of the claims in any way.

Example 1

In this example, two amino acid segments from hCG were prepared and then used to create a homeopathic remedy. The first amino acid segment includes the first twenty five amino acids starting at the N-terminal of the alpha subunit of hCG and has the following sequence (SEQ ID NO: 1): Ala-Pro-Asp-Val-Gln-Asp-Cys-Pro-Glu-Cys-Thr-Leu-Gln-Glu-Asn-Pro-Phe-Phe-Ser-Gln-Pro-Gly-Ala-Pro-Ile.

The second amino acid segment includes the last thirty amino acids ending at the C-terminal of the beta subunit of hCG and has the following sequence (SEQ ID No: 2): Gln-Asp-SerSer-Ser-Ser-Ser-Lys-Ala-Pro-Pro-Pro-Ser-Leu-Pro-Ser-Pro-Ser-Arg-Leu-Pro-Gly-Pro-Ser-Asp-Thr-Pro-Ile-Leu- Pro-Gln. These segments were selected because they are more biologically active and influential in comparison to the remainder of the hCG protein.

The first and second amino acid segments have molecular weights of 2705 g/mol and 3041 g/mol, respectively. The segments were synthesized at a cGMP facility using standard techniques for amino acid synthesis. Mass spectral analysis using the electrospray technique confirmed the accuracy of the molecular weights and that the purity of the amino acid segments was 97% to 98% with a solubility of 1 mg/ml in 5% $NH_4OH$ in water.

Each of the amino acid segments is lyophilized resulting in a dry white powder. The powder includes acetate counter-ions (OAc-) paired with positively charged residues. The acetate counter-ion also increases oral absorption of the material.

The first and second amino acid segments were used to make a variety of diluted formulations. The first amino acid segments were used to prepare various formulation using the following procedure. A mother tincture was prepared by mixing 10 mg of powder containing the first amino acid segments with 100 ml of 95% ethyl alcohol. The mother tincture was succussed 10 times to create a 4X potency.

The mother tincture was further diluted by mixing 100 ml of the mother tincture with 900 ml of 50% ethyl alcohol and succussed 10 times to create a 5X potency mixture. The 5X potency mixture was further diluted to prepare mixtures having potencies of 8X, 12X, 30X, 60X, and 200X. The 5X mixture was repeatedly diluted using a dilution ratio of 1:10 followed by 10 succussions until the desired potency was reached. A composite mixture was prepared by mixing 120 ml of each of the 8X, 12X, 30X, 60X, and 200X mixtures together.

The second amino acid segments were used to prepare various formulations using the following procedure. A mother tincture was prepared by mixing 10 mg of powder containing the second amino acid segments with 10 ml of water. The mother tincture was succussed 10 times to create a 3X potency.

The mother tincture was further diluted by missing 10 ml of the mother tincture with 90 ml of 50% ethyl alcohol and succussed 10 times to create a 4X potency mixture. 100 ml of the 4X mixture was added to 900 ml of 50% ethyl alcohol and succussed 10 times to create a 5X potency mixture.

The 5X mixture was further diluted to prepare mixtures having potencies of 8X, 12X, 30X, 60X, and 200X. The 5X mixture was repeatedly diluted using a dilution ratio of 1:10 followed by 10 succussions until the desired potency was reached. A composite mixture was prepared by mixing 120 ml of each of the 8X, 12X, 30X, 60X, and 200X mixtures together.

The mixtures above were then compounded with various other mixtures, including mixtures prepared from other materials, to produce a final formulation. Examples of the other mixtures that can be compounded with one or more of the amino acid mixtures above include: Brain Suis 8X, Hepar Suis 8X, Methylcobalamin 8X, Pancreas Suis 8X, Renal Suis 8X, Stomach Suis 8X, Asclepias Vincetoxicum 6X, 12X, and 30X, Echinacea 6X, 12X, and 30X, Hypothalamys Suis 6X, 12X, and 30X, Calcarea Carbonica 12X, 30X, and 60X, Gambogia 12X, 30X, and 60X, Gelsemium Sempervirens 12X, 30X, and 60X, Graphites 12X, 30X, and 60X, Nux Vomica 12X, 30X, and 60X, Phytolacca Decandra 12X, 30X, and 60X, 7-Keto DHEA 30X, ATP 30X, Glucagon 30X, Insulin 30X, Sarcolacticum Acidum 30X, Demineralized Water, 25% Ethyl Alcohol, and Proteus Bach 30C.

The amino acid mixtures above can be mixed together with each other and/or other mixtures in any desirable combination to produce a final formulation. The resulting mixtures can be further diluted and succussed until the desired potency is achieved.

Example 2

In this example, an amino acid segment is prepared that includes the first twenty five amino acids starting at the N-terminal of the hCG alpha subunit followed by the last thirty five amino acids ending at the C-terminal of the hCG beta subunit.

Homeopathic formulations are prepared by serially diluting the samples above to a potency of 60X. The samples are administered to humans via oral dosage by tablet, capsule, gelcap, liquid or other common method of administration. The samples are also incorporated into food products such as an energy bar, cereal, beverage, energy drink, etc.

Illustrative Embodiments

Reference is made in the following to a number of illustrative embodiments of the disclosed subject matter. The following embodiments illustrate only a few selected embodiments that may include one or more of the various features, characteristics, and advantages of the disclosed subject matter. Accordingly, the following embodiments should not be considered as being comprehensive of all of the possible embodiments.

The concepts and aspects of one embodiment may apply equally to one or more other embodiments or may be used in combination with any of the concepts and aspects from the other embodiments. Any combination of any of the disclosed subject matter is contemplated.

In one embodiment, a method comprises: mixing an amino acid segment and a diluting agent to form a mixture; and serially diluting at least a portion of the mixture to produce a diluted formulation. The peptide sequence of the amino acid segment is the same as a portion of a longer peptide sequence found in a naturally occurring material.

The naturally occurring material may include a peptide hormone, protein, or other suitable material. For example, the naturally occurring material can include human chorionic gonadotropin, follicle-stimulating hormone, luteinizing hormone, thyroid-stimulating hormone, human growth hormone, insulin, leptin, angiotensin, cholecystokinin, and/or ghrelin. In one embodiment, the naturally occurring material includes human chorionic gonadotropin.

The peptide sequences of at least 50% w/w (or 5% w/w to 100% w/w including any amount in between) of the amino acid segments in the mixture are the same as a portion of one or more longer peptide sequences found in one or more naturally occurring materials. The peptide sequences of at least 50% w/w (or 5% w/w to 100% w/w including any amount in between) of the amino acid segments in the mixture are the same as a portion of one or more longer peptide sequences found in a single naturally occurring material. The portion of the longer peptide sequence can include a terminal end.

Serially diluting at least a portion of the mixture may include producing successive, increasingly dilute mixtures and vigorously mixing each increasingly dilute mixture. Serially diluting at least a portion of the mixture may include producing successive, increasingly dilute mixtures using the same dilution ratio for each increasingly dilute mixture.

The mixture can be serially diluted using an average dilution ratio of no more than approximately 1:5. The mixture can be serially diluted at least three times. The concentration of the one or more amino acid segments in the diluted formulation may be no more than $1 \times 10^{-3}$ w/w or v/v. The mixture can be serially diluted with water, alcohol, glycerin, lactose, and/or sucrose.

In another embodiment, a method comprises: mixing an amino acid segment and a diluting agent to form a mixture; repeatedly diluting at least a portion of the mixture to produce successive, increasingly dilute mixtures; and succussing each increasingly dilute mixture. The peptide sequence of the amino acid segment is the same as a portion of a longer peptide sequence found in a naturally occurring material.

The naturally occurring material may include a peptide hormone, protein, or other suitable material. For example, the naturally occurring material can include human chorionic gonadotropin, follicle-stimulating hormone, luteinizing hormone, thyroid-stimulating hormone, human growth hormone, insulin, leptin, angiotensin, cholecystokinin, and/or ghrelin. In one embodiment, the naturally occurring material includes human chorionic gonadotropin.

The peptide sequences of at least 50% w/w (or 5% w/w to 100% w/w including any amount in between) of the amino acid segments in the mixture are the same as a portion of one or more longer peptide sequences found in one or more naturally occurring materials. The peptide sequences of at least 50% w/w (or 5% w/w to 100% w/w including any amount in between) of the amino acid segments in the mixture are the same as a portion of one or more longer peptide sequences found in a single naturally occurring material. The portion of the longer peptide sequence can include a terminal end.

Serially diluting at least a portion of the mixture may include producing successive, increasingly dilute mixtures and vigorously mixing each increasingly dilute mixture. Serially diluting at least a portion of the mixture may include producing successive, increasingly dilute mixtures using the same dilution ratio for each increasingly dilute mixture.

The mixture can be serially diluted using an average dilution ratio of no more than approximately 1:5. The mixture can be serially diluted at least three times. The concentration of the one or more amino acid segments in the diluted formulation may be no more than $1 \times 10^{-3}$ w/w or v/v. The mixture can be serially diluted with water, alcohol, glycerin, lactose, and/or sucrose.

In another embodiment, a homeopathic remedy comprises: a container; a formulation inside the container; and a label attached to the container. The label indicates that the formulation is an amino acid segment at a potency of at least 1X. The peptide sequence of the amino acid segment is the same as a portion of a longer peptide sequence found in a naturally occurring material.

The label may indicate that the formulation is an amino acid segment at a potency of at least 3X. The label may also indicate that the formulation is homeopathic in nature. The formulation can be a liquid, pellet, tablet, or capsule.

In another embodiment, a method comprises administering a diluted formulation prepared using one or more amino acid segments. The one or more amino acid segments can be either natural or synthesized and can function as a therapeutic agent for women's and men's health to promote, prevent, treat, support, or ameliorate: infertility, weight control, obesity, appetite control, diabetes, thyroid disease, hypertension or blood pressure control, anti-aging, and growth and development.

The one or more amino acid segments can include a portion of the N-terminal segment of the hCG alpha subunit and at least one or more other segments such as the C-terminal segment of the hCG beta subunit.

The diluted formulation may decrease body weight in mammals, decrease appetite in mammals, decrease blood sugar levels in mammals, increase thyroid hormone levels in mammals, modulate blood pressure in mammals, stimulate growth and development in mammals, and/or stimulate reproductive function.

The formulation may be administered orally as a tablet, capsule, gelcap, liquid, or other common method. The therapeutic agent can also be administered via injection by a subcutaneous, intra-muscular, or intravenous route. The therapeutic agent can also be incorporated into food products such as an energy bar, cereal, beverage, energy drink, dip, yogurt, gum, candy, etc.

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure the term shall mean," etc.).

References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope.

The subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be given their broadest interpretation in view of the prior art and the meaning of the claim terms.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

The term "and/or" shall also be interpreted to be inclusive (e.g., "x and/or y" means one or both x or y). In situations where "and/or" or "or" are used as a conjunction for a group of three or more items, the group should be interpreted to include one item alone, all of the items together, or any combination or number of the items. Moreover, terms used in the specification and claims such as have, having, include, and including should be construed to be synonymous with the terms comprise and comprising.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

All ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

The invention claimed is:

1. A method comprising:
   mixing an amino acid fragment and a diluting agent to form a mixture; and
   serially diluting at least a portion of the mixture to produce a diluted formulation having a concentration of the amino acid fragment that is no more than $1 \times 10^{-10}$ w/w;
   wherein the amino acid fragment includes a peptide sequence of at least five amino acids that is the same as the N-terminal end of the beta subunit of human chorionic gonadotropin; and
   wherein the amino acid fragment is not the same as the complete peptide sequence of either the alpha or beta subunit of human chorionic gonadotropin.

2. The method of claim 1 wherein the peptide sequence includes at least ten amino acids and is the same as the N-terminal end of the beta subunit of human chorionic gonadotropin.

3. The method of claim 1 wherein the peptide sequence includes at least fifteen amino acids and is the same as the N-terminal end of the beta subunit of human chorionic gonadotropin.

4. The method of claim 1 wherein the peptide sequence includes at least twenty amino acids and is the same as the N-terminal end of the beta subunit of human chorionic gonadotropin.

5. The method of claim 1 wherein the peptide sequence is a first peptide sequence, the amino acid fragment including a second peptide sequence of at least five amino acids that is the same as a terminal end of the alpha subunit of human chorionic gonadotropin.

6. The method of claim 5 wherein the second peptide sequence is the same as the N-terminal end of the alpha subunit of human chorionic gonadotropin.

7. The method of claim 5 wherein the second peptide sequence includes at least ten amino acids and is the same as the terminal end of the alpha subunit of human chorionic gonadotropin.

8. The method of claim 1 wherein at least 50% w/w of the amino acid fragments in the mixture each include a peptide sequence of at least five amino acids that is the same as the N-terminal end of the beta subunit of human chorionic gonadotropin, and wherein the at least 50% w/w of the amino acid fragments are not the same as the complete peptide sequence of either the alpha or beta subunit of human chorionic gonadotropin.

9. The method of claim 1 wherein serially diluting at least a portion of the mixture includes producing successive, increasingly dilute mixtures and vigorously mixing each increasingly dilute mixture.

10. The method of claim 1 wherein serially diluting at least a portion of the mixture includes producing successive, increasingly dilute mixtures using the same dilution ratio for each increasingly dilute mixture.

11. The method of claim 1 wherein the mixture is serially diluted using an average dilution ratio of no more than approximately 1:5.

12. The method of claim 1 wherein the mixture is serially diluted at least three times.

13. The method of claim 1 wherein the potency of the diluted formulation is at least 20V, 10X, or 5C.

14. A method comprising:
mixing an amino acid fragment and a diluting agent to form a mixture;
repeatedly diluting at least a portion of the mixture to produce successive, increasingly dilute mixtures including a dilute mixture having a concentration of the amino acid fragment that is no more than $1\times10^{-10}$ w/w; and
succussing each increasingly dilute mixture;
wherein the amino acid fragment includes a peptide sequence of at least five amino acids that is the same as the N-terminal end of the beta subunit of human chorionic gonadotropin; and
wherein the amino acid fragment is not the same as the complete peptide sequence of either the alpha or beta subunit of human chorionic gonadotropin.

15. The method of claim 14 wherein the peptide sequence includes at least ten amino acids and is the same as the N-terminal end of the beta subunit of human chorionic gonadotropin.

16. The method of claim 14 wherein the peptide sequence includes at least fifteen amino acids and is the same as the N-terminal end of the beta subunit of human chorionic gonadotropin.

17. The method of claim 14 wherein the peptide sequence includes at least twenty amino acids and is the same as the N-terminal end of the beta subunit of human chorionic gonadotropin.

18. The method of claim 14 wherein the peptide sequence is a first peptide sequence, the amino acid fragment including a second peptide sequence of at least five amino acids that is the same as a terminal end of the alpha subunit of human chorionic gonadotropin.

19. The method of claim 14 wherein at least 50% w/w of the amino acid fragments in the mixture each include a peptide sequence of at least five amino acids that is the same as the N-terminal end of the beta subunit of human chorionic gonadotropin, and wherein the at least 50% w/w of the amino acid fragments are not the same as the complete peptide sequence of either the alpha or beta subunit of human chorionic gonadotropin.

20. The method of claim 14 wherein the same dilution ratio is used to produce each increasingly dilute mixture.

21. The method of claim 14 wherein each increasingly dilute mixture is diluted using an average dilution ratio of no more than approximately 1:5.

22. The method of claim 14 wherein repeatedly diluting at least a portion of the first mixture produces at least three increasingly dilute mixtures.

23. A packaged formulation comprising:
a container;
a homeopathic formulation inside the container; and
a label attached to the container;
wherein the homeopathic formulation is produced by the method recited in claim 1.

24. The packaged formulation of claim 23 wherein the peptide sequence includes at least ten amino acids and is the same as the N-terminal end of the beta subunit of human chorionic gonadotropin.

25. The packaged formulation of claim 23 wherein the peptide sequence includes at least fifteen amino acids and is the same as the N-terminal end of the beta subunit of human chorionic gonadotropin.

26. The packaged formulation of claim 23 wherein the peptide sequence includes at least twenty amino acids and is the same as the N-terminal end of the beta subunit of human chorionic gonadotropin.

27. The packaged formulation of claim 23 wherein the peptide sequence is a first peptide sequence, the amino acid fragment including a second peptide sequence of at least five amino acids that is the same as a terminal end of the alpha subunit of human chorionic gonadotropin.

28. The packaged formulation of claim 27 wherein the second peptide sequence is the same as the N-terminal end of the alpha subunit of human chorionic gonadotropin.

29. The packaged formulation of claim 27 wherein the second peptide sequence includes at least ten amino acids and is the same as the terminal end of the alpha subunit of human chorionic gonadotropin.

30. The packaged formulation of claim 23 wherein the homeopathic formulation is liquid.

31. The packaged formulation of claim 23 wherein the homeopathic formulation is in the form of a pellet, tablet, or capsule.

* * * * *